(12) United States Patent
Shiran et al.

(10) Patent No.: US 11,464,488 B2
(45) Date of Patent: Oct. 11, 2022

(54) METHODS AND SYSTEMS FOR A MEDICAL GRADING SYSTEM

(71) Applicant: General Electric Company, Schenectady, NY (US)

(72) Inventors: Carmit Shiran, Haifa (IL); Mor Vardi, Haifa (IL)

(73) Assignee: General Electric Company, Schenectady, NY (US)

( * ) Notice: Subject to any disclaimer, the term of this patent is extended or adjusted under 35 U.S.C. 154(b) by 451 days.

(21) Appl. No.: 16/234,276

(22) Filed: Dec. 27, 2018

(65) Prior Publication Data

US 2020/0205783 A1 Jul. 2, 2020

(51) Int. Cl.
*A61B 8/00* (2006.01)
*G06F 3/04817* (2022.01)
*G06F 3/0482* (2013.01)

(52) U.S. Cl.
CPC .............. *A61B 8/465* (2013.01); *A61B 8/463* (2013.01); *A61B 8/469* (2013.01); *G06F 3/0482* (2013.01); *G06F 3/04817* (2013.01)

(58) Field of Classification Search
CPC ......... A61B 8/465; A61B 8/469; A61B 8/463; A61B 8/54; A61B 8/468; A61B 8/466; A61B 8/467; A61B 8/52; G06F 3/04817; G06F 3/0482
See application file for complete search history.

(56) References Cited

U.S. PATENT DOCUMENTS

| 5,920,317 A | 7/1999 | McDonald | |
|---|---|---|---|
| 5,938,607 A | 8/1999 | Jago et al. | |
| 6,063,030 A * | 5/2000 | Vara | A61B 8/00 600/437 |
| 8,315,884 B2 * | 11/2012 | Snell | G16H 40/63 705/2 |
| 2013/0325510 A1 * | 12/2013 | Vendrell | G16H 30/40 705/3 |
| 2014/0164968 A1 * | 6/2014 | Aalami | G16H 40/63 715/771 |
| 2015/0278483 A1 * | 10/2015 | Pruitt | G16H 10/60 705/3 |

* cited by examiner

Primary Examiner — Hien N Nguyen
(74) Attorney, Agent, or Firm — McCoy Russell LLP

(57) ABSTRACT

Various methods and systems are provided for graphical grading of medical findings during a diagnostic imaging exam. In one example, a method includes displaying an acquired medical image on a display area of a display device, displaying a virtual anatomical diagram on the display area adjacent to the ultrasound medical image, responsive to selection of an anatomical region from the anatomical diagram, displaying a plurality of icons representing graded diagnostic findings associated with the anatomical region, and responsive to selection of an icon of the plurality of icons, storing the ultrasound medical image in permanent memory.

15 Claims, 13 Drawing Sheets

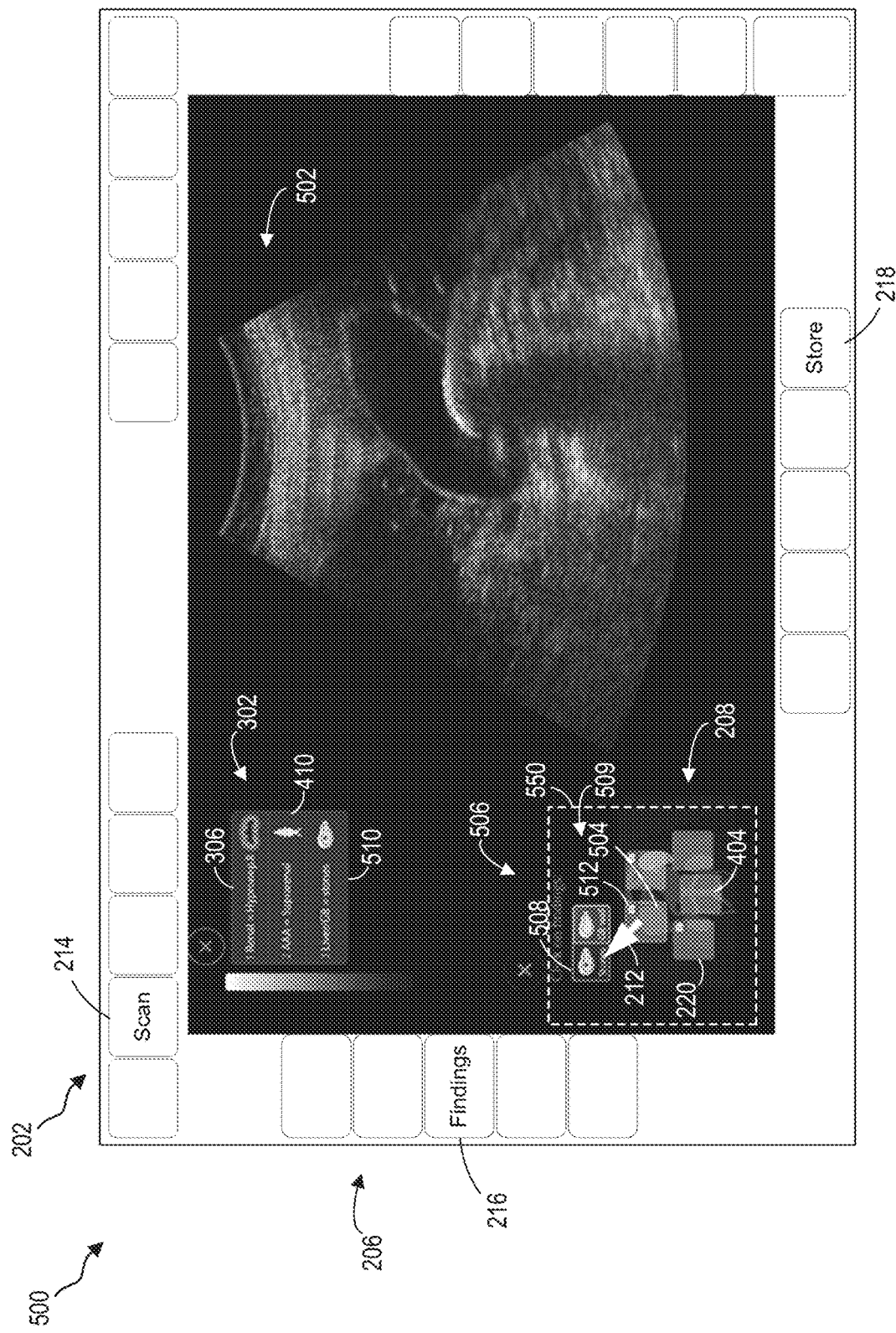

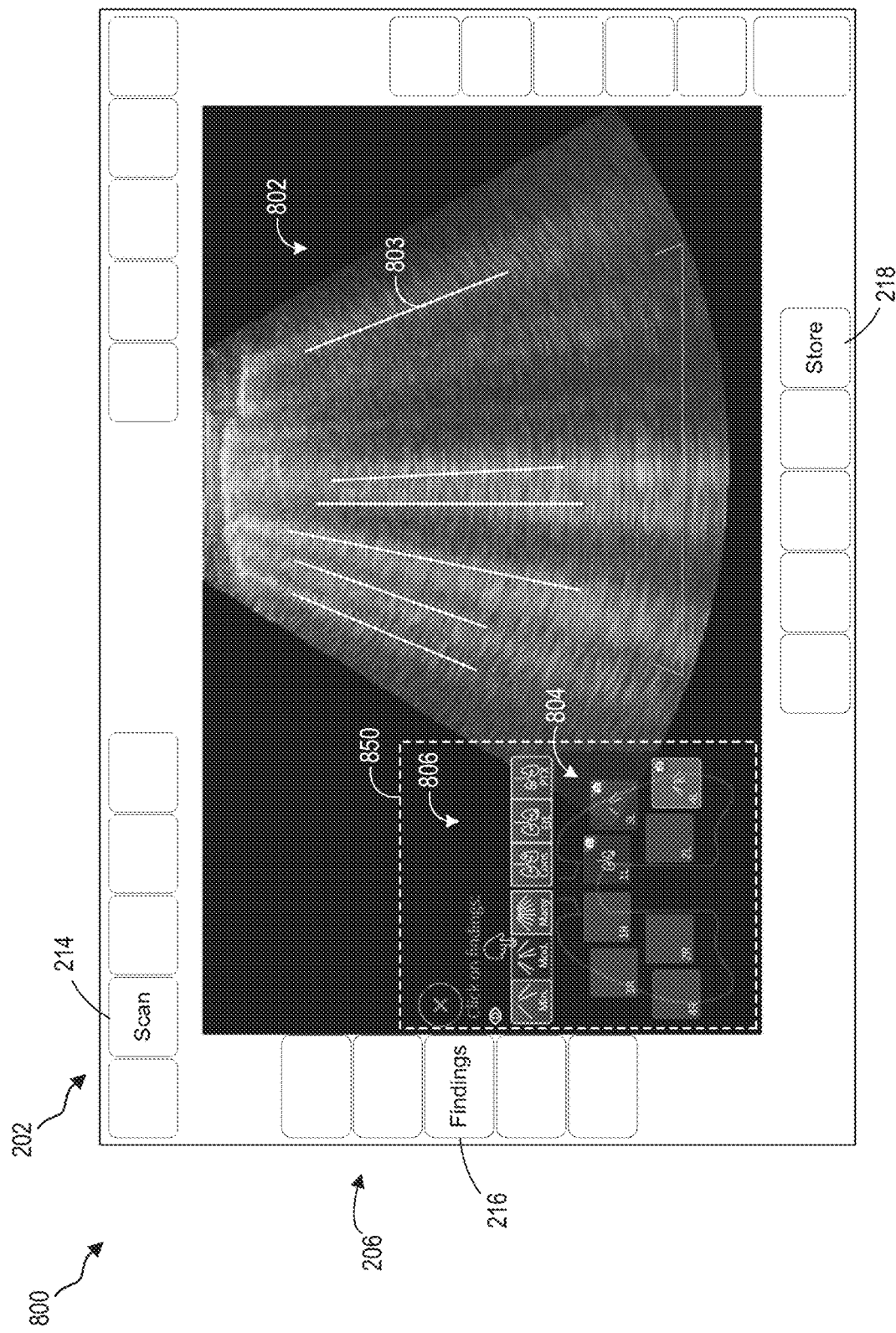

METHODS AND SYSTEMS FOR A MEDICAL GRADING SYSTEM

FIELD

Embodiments of the subject matter disclosed herein relate to medical imaging, and more particularly to presenting diagnostic findings during a medical imaging exam.

BACKGROUND

An ultrasound imaging system typically includes an ultrasound probe that is applied to a patient's body and a workstation or device that is operably coupled to the probe. The probe may be controlled by an operator of the system and is configured to transmit and receive ultrasound signals that are processed into an ultrasound image by the workstation or device. The workstation or device may display the ultrasound images as part of a graphical user interface on a display device. The graphical user interface may include virtual graphical buttons that allow the operator to access various functions of the software program used to operate the ultrasound system. In one example, the graphical user interface may include options for selecting a specific region of a patient's anatomy that has been scanned by the ultrasound probe. The operator may enter input via the graphical user interface to associate evaluation of an ultrasound scan with an image file for the patient.

BRIEF DESCRIPTION

In one embodiment, a method includes displaying an acquired medical image on a display area of a display device, displaying a virtual anatomical diagram on the display area adjacent to the ultrasound medical image, responsive to selection of an anatomical region from the anatomical diagram, displaying a plurality of icons representing graded diagnostic findings associated with the anatomical region, and responsive to selection of an icon of the plurality of icons, storing the ultrasound medical image in permanent memory.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below:

FIG. 5A shows a fourth view of the display area of the ultrasound imaging system;

FIG. 8A shows a fifth view of the display area of the ultrasound imaging system.

DETAILED DESCRIPTION

Figure 1:
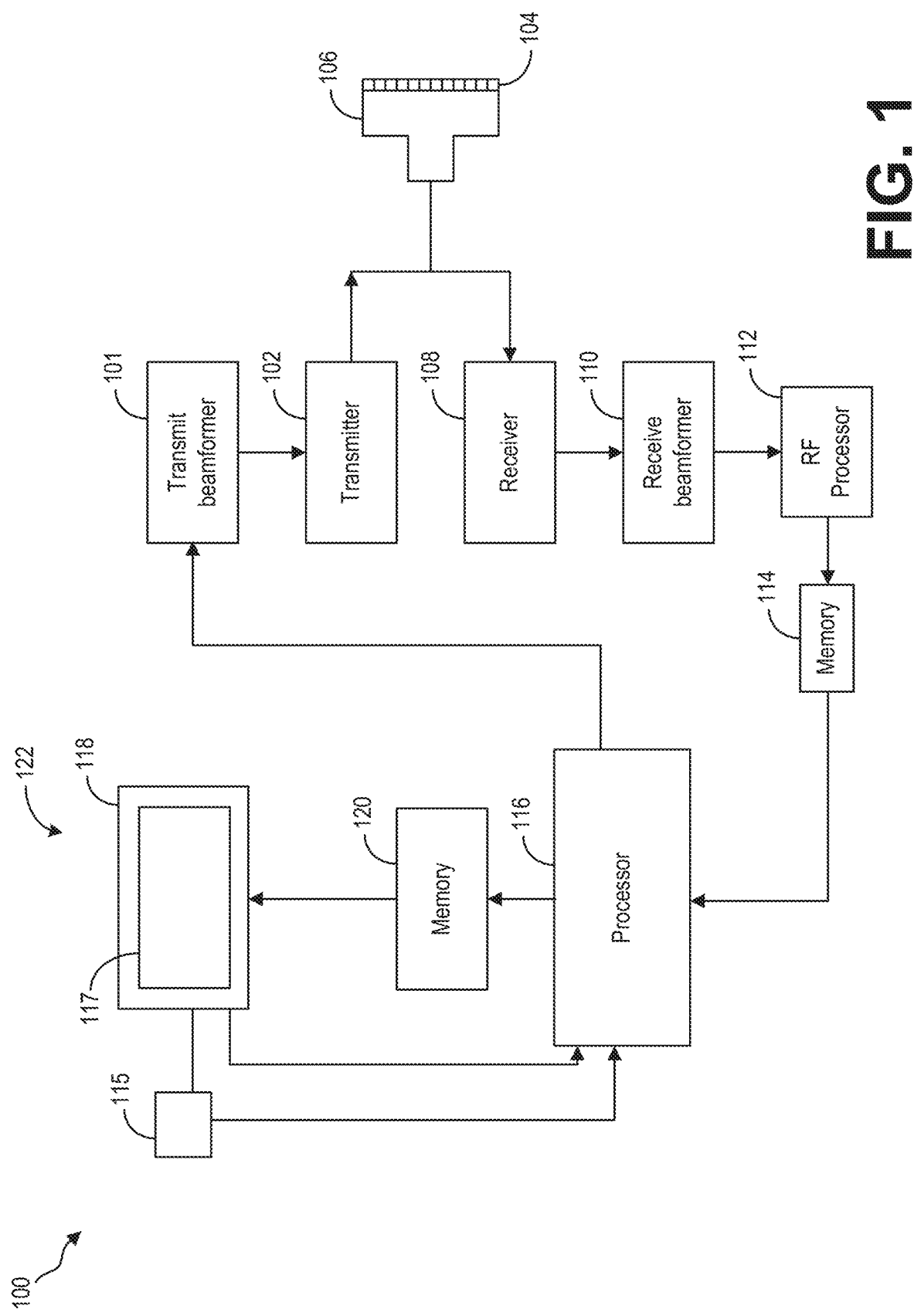
FIG. 1 shows an example ultrasound imaging system according to an embodiment.
Figure 6:
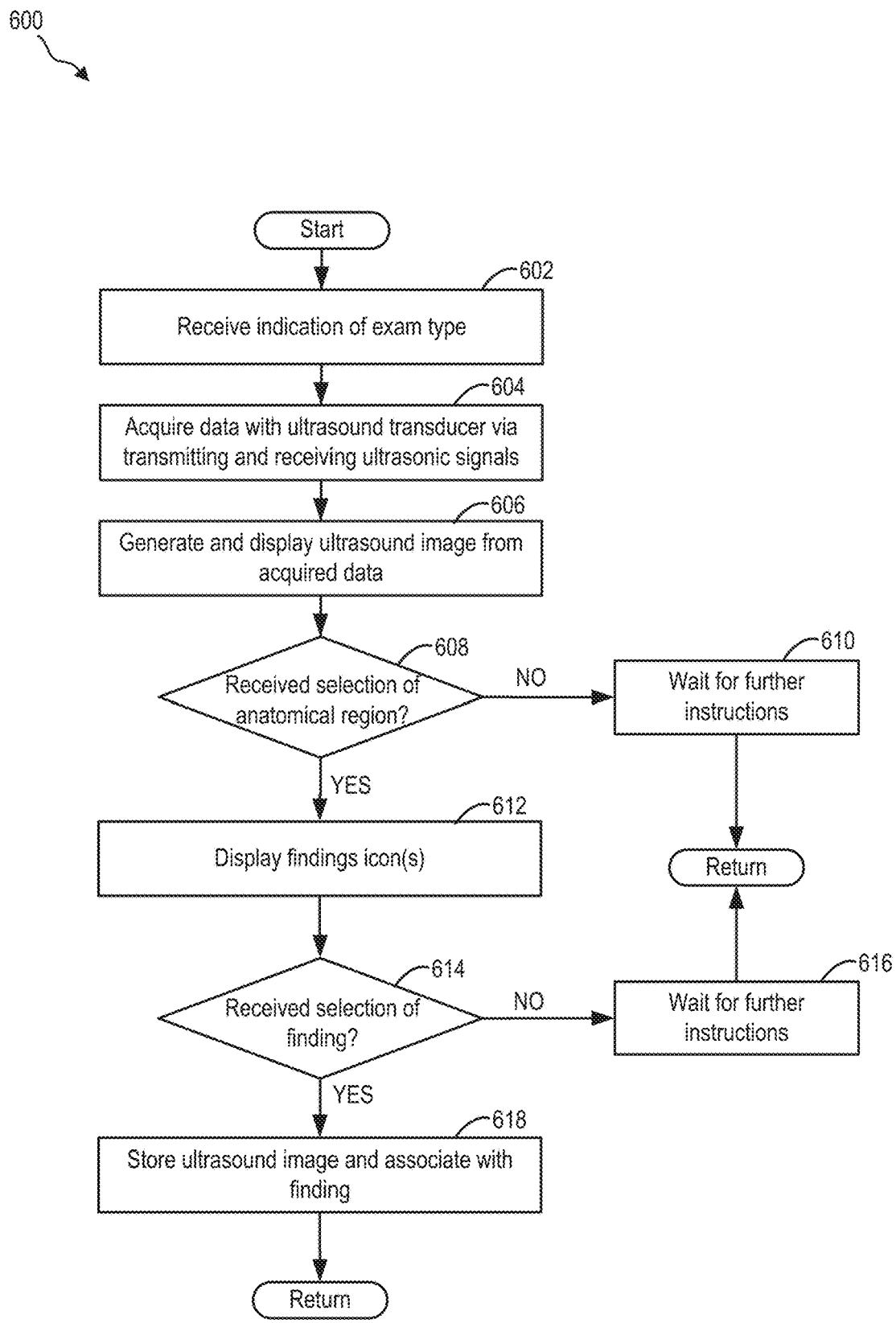
FIG. 6 shows a flow chart illustrating an example method for saving an ultrasound image to a memory according to an embodiment.
Figure 7:
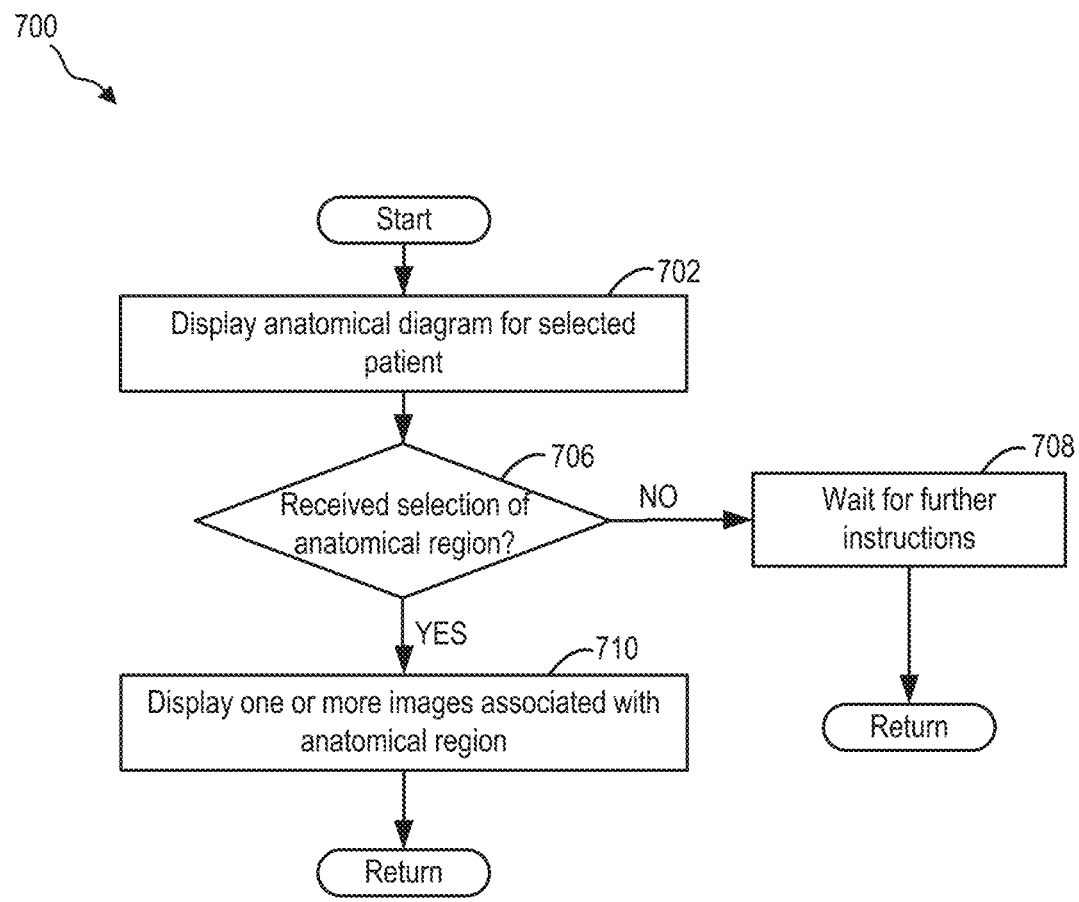
FIG. 7 shows a flow chart illustrating an example method for retrieving an ultrasound image from a memory according to an embodiment.

The following description relates to various embodiments of medical imaging, such as the ultrasound imaging system shown in FIG. 1. In particular, systems and methods simplifying storage of medical images in memory according to diagnostic grading are provided. The medical imaging system may include a display device with a display area presenting data acquired by an imager, such as an ultrasound transducer, as an image. The display area may, in addition to the medical image, show a plurality of graphical control buttons allowing an operator to command storage of the image in memory, as shown in FIGS. 2A-5C, 8A, and 8B. The entire display area is shown in FIGS. 2A, 3A, 4A, 5A, and 8A in different views while FIGS. 2B, 3B, 4B-4C, 5B-5C, and 8B depict expanded views of select regions of the display area. The plurality of control buttons and icons may include an anatomical diagram, representing regions of a patient's anatomy. Each region of the anatomical diagram may be linked to one or more diagnostic findings as well as grading levels for each type of finding. Examples of diagnostic findings associated with specific anatomical regions displayed on the display area are depicted in FIGS. 2A-5C, 8A, and 8B. An example of a routine for storing an ultrasound image according to the diagnostic finding into a patient's digital medical archives is shown in FIG. 6. An example of a complementary routine for retrieval of the ultrasound image from the digital medical archives is shown in FIG. 7. In this way, a number of steps performed by the operator to store the ultrasound image is reduced and simplified, thereby increasing workflow and decreasing a likelihood of incorrect assignment of the image to a digital folder.

FIGS. 1-5C, 8A, and 8B show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space there-between and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

FIG. 1 illustrates a block diagram of a system 100 according to one embodiment. In the illustrated embodiment, the system 100 is an imaging system, and more specifically, an ultrasound imaging system. However, it is understood that embodiments set forth herein may be implemented using other types of medical imaging modalities (e.g., MR, CT, PET/CT, SPECT, and so on). Furthermore, it is understood that other embodiments do not actively acquire medical images. Instead, embodiments may retrieve image data that was previously acquired by an imaging system and analyze the image data as set forth herein. As shown, the system 100 includes multiple components. The components may be coupled to one another to form a single structure, may be separate but located within a common room, or may be remotely located with respect to one another. For example, one or more of the modules described herein may operate in a data server that has a distinct and remote location with respect to other components of the system 100, such as a probe and user interface. Optionally, in the case of ultrasound systems, the system 100 may be a unitary system that is capable of being moved (e.g., portably) from room to room. For example, the system 100 may include wheels or be transported on a cart, or may comprise a handheld device.

In the illustrated embodiment, the system 100 includes a transmit beamformer 101 and a transmitter 102 that drive elements 104, such as piezoelectric crystals, within a transducer array, or probe, 106 to emit pulsed ultrasonic signals into a body or volume (not shown) of a subject. The elements 104 and the probe 106 may have a variety of geometries. For example, the probe 106 may be a one-dimensional transducer array probe or a two-dimensional matrix transducer array probe. The ultrasonic signals are back-scattered from structures in the body, such as blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that performs beamforming and outputs an RF signal or ultrasound data. The RF signal or ultrasound data is then provided to an RF processor 112 that processes the RF signal. Alternatively, the RF processor 112 may include a complex demodulator (not shown) that demodulates the RF signal to form IQ data pairs representative of the echo signals. The RF or IQ signal data may then be provided directly to a memory 114 for storage (for example, temporary storage).

According to some embodiments, the probe 106 may contain electronic circuitry to do all or part of the transmit and/or the receive beamforming. For example, all or part of the transmit beamformer 101, the transmitter 102, the receiver 108, and the receive beamformer 110 may be situated within the probe 106. The terms "scan" or "scanning" may also be used in this disclosure to refer to acquiring data through the process of transmitting and receiving ultrasonic signals. The term "data" may be used in this disclosure to refer to either one or more datasets acquired with an ultrasound imaging system.

The system 100 also includes a controller or processor 116 configured to control operation of the system 100, including the transmit beamformer 101, the transmitter 102, the receiver 108, and the receive beamformer 110. The processer 116 is in electronic communication with the probe 106. For purposes of this disclosure, the term "electronic communication" may be defined to include both wired and wireless communications. The processor 116 may control the probe 106 to acquire data. The processor 116 controls which of the elements 104 are active and the shape of a beam emitted from the probe 106.

The processor 116 may include a central processor (CPU) according to an embodiment. According to other embodiments, the processor 116 may include other electronic components capable of carrying out processing functions, such as a digital signal processor, a field-programmable gate array (FPGA), or a graphic board. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphic board.

The processor 116 is adapted to perform one or more processing operations according to a plurality of selectable ultrasound modalities on the data. The data may be processed in real-time during a scanning session as the echo signals are received. For the purposes of this disclosure, the term "real-time" is defined to include a procedure that is performed without any intentional delay. To that end, the processor 116 may include an image processing module (not shown) that receives image data (e.g., ultrasound signals in the form of RF signal data or IQ data pairs) and processes image data. For example, the image processing module may process the ultrasound signals to generate slices or frames of ultrasound information (e.g., ultrasound images) for displaying to the operator. When the system 100 is an ultrasound system, the image processing module may be configured to perform one or more processing operations according to a plurality of selectable ultrasound modalities on the acquired ultrasound information. By way of example only, the ultrasound modalities may include color-flow, acoustic radiation force imaging (ARFI), B-mode, A-mode, M-mode, spectral Doppler, acoustic streaming, tissue Doppler, C-scan, and elastography. The generated ultrasound images may be two-dimensional (2D) or three-dimensional (3D). When multiple two-dimensional images are obtained, the image processing module may also be configured to stabilize or register the images. The image lines and/or volumes are stored and timing information indicating a time at which the data was acquired in memory may be recorded. The modules may include, for example, a scan conversion module to perform scan conversion operations to convert the image volumes from beam space coordinates to display space coordinates. A video processor module may be provided that reads the image volumes from a memory and displays an image in real time while a procedure is being carried out on a patient. A video processor module may store the images in an image memory, from which the images are read and displayed.

As mentioned above, acquired ultrasound information may be processed in real-time during an imaging session (or scanning session) as the echo signals are received. Additionally or alternatively, the ultrasound information may be stored temporarily in a buffer or memory 114 during an imaging session and processed in less than real-time in a live or off-line operation. An image memory 120 is included for storing processed slices of acquired ultrasound information that are not scheduled to be displayed immediately. The image memory 120 may comprise any known data storage medium, for example, a permanent storage medium, removable storage medium, and the like. Additionally, the image memory 120 may comprise a non-transitory storage medium.

In operation, an ultrasound system may acquire data, for example, volumetric data sets by various techniques (e.g., 3D scanning, real-time 3D imaging, volume scanning, 2D scanning with probes having positioning sensors, freehand scanning using a voxel correlation technique, scanning using 2D or matrix array probes, and the like). Ultrasound images of the system 100 may be generated from the acquired data at the processor 116 and displayed to the operator or user on a display device 118.

The processor 116 is operably connected to a user interface 122 that enables an operator to control at least some of the operations of the system 100. The user interface 122 may include hardware, firmware, software, or a combination thereof that enables an individual (e.g., an operator) to directly or indirectly control operation of the system 100 and the various components thereof. As shown, the user interface 122 includes a display device 118 having a display area 117. In some embodiments, the user interface 122 may also include one or more user interface input devices 115, such as a physical keyboard, mouse, and/or touchpad. In some embodiments, the user interface input device 115 comprises a touchpad communicatively coupled to the processor 116 and the display device 118, such that when a user moves a finger, glove, or stylus across the face of the touchpad, a cursor atop the display area 117 moves in a corresponding manner. In other embodiments, the display device 118 comprises a touch-sensitive display (e.g., a touchscreen) that can detect a presence of a touch from the operator on the display area 117 and can also identify a location of the touch in the display area 117. The touch may be applied, for example, by at least one of an individual's hand or finger, a glove, a stylus, and the like. As such, the touch-sensitive display may also be characterized as an input device that is configured to receive inputs from the operator. The display device 118 also communicates information from the processor 116 to the operator by displaying the information to the operator. The display device 118 is configured to present information to the operator during the imaging session. For example, the information presented may include ultrasound images, graphical elements, user-selectable elements, and other information (e.g., administrative information, personal information of the subject, and the like).

Information displayed to the operator, via the display device, may include details pertaining to a state of health of a particular anatomical region of a patient. Thus, it may be desirable to store the information, presented as graphical images, in a file designated to the patient. In conventional systems, storing ultrasound images onto a memory, e.g., the image memory 120 of FIG. 1 or a central server, may be achieved by performing a string of actions. More specifically, for medical findings, an operator such as a physician or sonographer may annotate one or more images during or after an exam with a medical finding, such as the presence or absence of diagnostic features of medical relevance (e.g., gallstones) and/or a grade/level of diagnostic features. To select a finding, the operator may navigate through multiple layers of menus displayed on a display device. For example, the operator may select a findings button from a graphical user interface displayed on the display device, which may cause a first menu to be displayed. The operator may navigate through the first menu to select an appropriate class of findings, which may cause a list of findings within that class to be displayed. The operator may then navigate through and select a desired finding, which in some examples may cause grades of that finding to be displayed. Once the operator selects the desired finding and/or grade, the operator may then select another button to save the finding and image. This process of saving the finding may lead to an increased likelihood of navigating to an incorrect location by clicking on an incorrect selectable element, and may also be time-consuming. In some examples, inefficient finding selection and image storage may delay diagnosis of the patient's health.

Furthermore, subsequent retrieval of the information may be convoluted and similarly time-consuming. The operator may search through two or more layers of menus before locating a target image displaying a specific finding. In addition, displaying multiple images showing more than one finding assigned to the patient may further increase an amount of time spent on compiling imaging results for the patient.

Thus, according to embodiments disclosed herein, the above issues may be addressed by configuring a display area of a medical imaging system, such as an ultrasound imaging system, with a graphical anatomical representation that represents one or more anatomical regions of a patient. A user may select an anatomical region of the graphical anatomical representation, and in response, one or more medical findings associated with the selected region may be displayed. If the medical image currently being displayed exhibits one of the displayed findings, the user may then select one of the findings, and the acquired medical image may be saved to a memory. The memory may be permanent memory, such as a server or other device associated with a medical facility (e.g., PACS). When the image is saved, the image may be associated with the finding, e.g., the finding may be included in a header or other meta-data of the image, the image may be annotated with the finding and the image may be saved along with the annotation, etc. In this way, once an anatomical region is selected, the user may select a finding using only a single input.

The stored image may be similarly retrieved, by selecting the displayed finding. A specific image for a finding may also be located and accessed by a single input, thereby decreasing an amount of time for retrieving medical imaging information and decreasing an amount of time for providing a medical diagnosis to the patient. Details of the system and method for efficient image storage and retrieval is described further below, with reference to FIGS. 2-5C, 8A, and 8B.

Figure 2A:
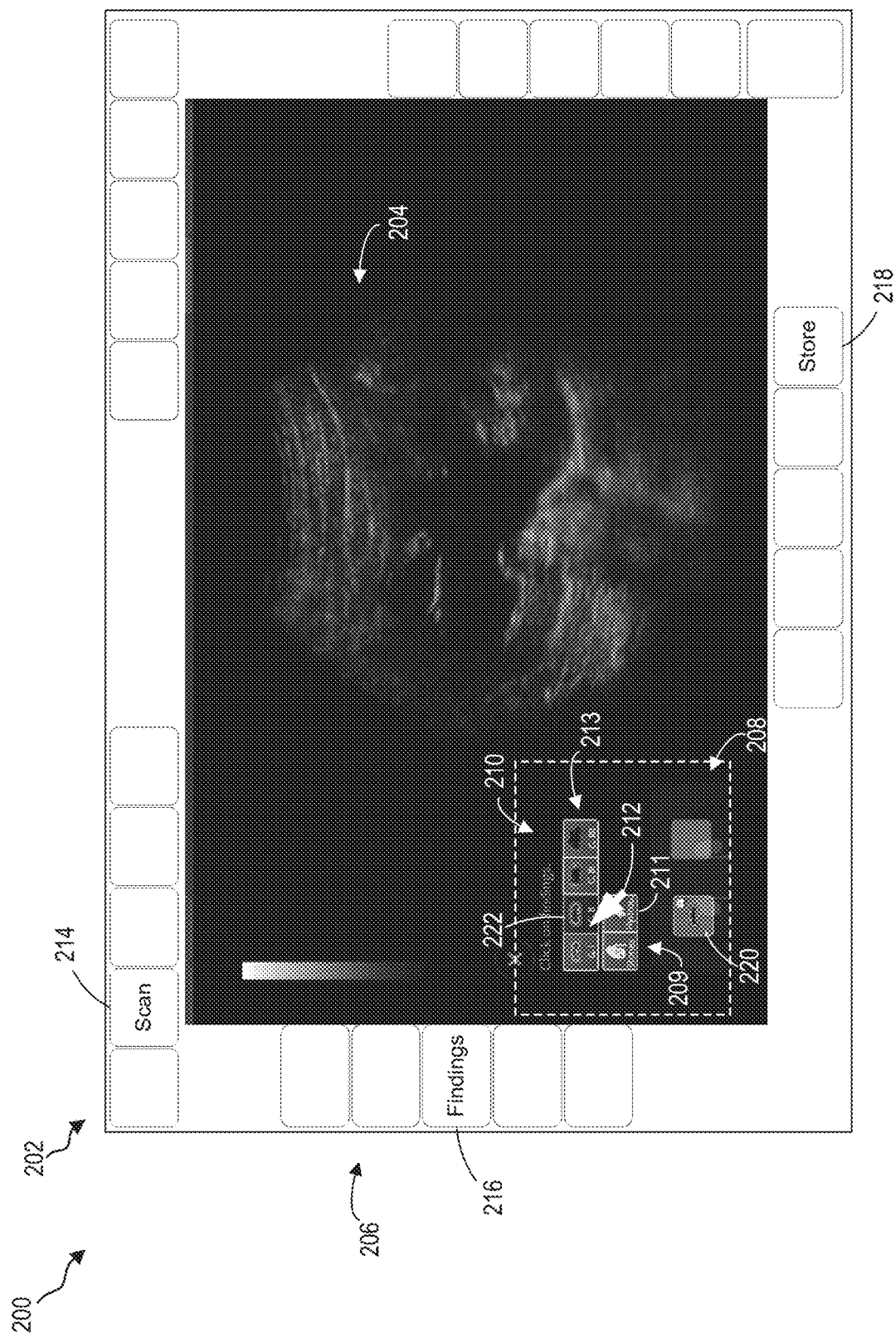
FIG. 2A shows a first view of a display area of an ultrasound imaging system according to an embodiment.

A display device for an ultrasound imaging system may have a display area, as described above, presenting information obtained from an ultrasound transducer as graphical images. A first view 200 of an example of a display area 202 of an ultrasound imaging system is depicted in FIG. 2A. The display area 202 is also shown in FIGS. 3A-5C, 8A, and 8B with variations in graphically displayed buttons and icons appearing in the display area 202. In one example, the display area 202 is a non-limiting example of the display area 117 of the display device 118 shown in FIG. 1, and thus display area 202 is part of a display device operably coupled to a computing device that includes a processor and memory, such as display device 118, processor 116, and memory 120 of FIG. 1.

The display area 202 shows a first image 204 in a central region of the display area 202, a plurality of control buttons 206 arranged around a periphery of the first diagnostic image 204, an anatomical diagram 208 positioned at a lower left corner of the display area 202, and a first set of findings icons 210 oriented above the anatomical diagram 208. The ultrasound imaging system may be configured to save acquired ultrasound images in an archive stored on a local memory of the ultrasound imaging system, with reference to the memory 120 of FIG. 1. In other examples, the archive may be located on a system network or server, such as a picture archiving and communication system (PACS). The ultrasound images may be stored on one or a combination of the storage options, e.g., saved to both the local memory and to the PACS. The display area 202 further includes a cursor 212, controlled by an operator via an input device such as a mouse or a touchpad. In other examples, the display area 202 may be a touch screen and not include the cursor 212. In such an implementation, the operator may directly contact the display area 202 with, for example, a finger, to facilitate effects as described further below.

The plurality of control buttons 206 may include a Scan button 214, a Findings button 216, and a Store button 218. The Scan button 214, when selected, e.g., clicked on with the cursor 212 or tapped with the operator's finger if the display area 202 is a touch screen, may activate the ultrasound transducer to enable ultrasonic scanning of the patient. The Findings button 216 may initiate display of a list of possible medical findings determined through ultrasound imaging, the findings associated with a specific anatomical region. The Store button 218, upon selection, may command saving of the displayed diagnostic image 204 to a location in memory.

To facilitate expedited selection of findings and archiving of desired images, a graphical grading system may be displayed in display area 202. The graphical grading system includes an anatomical diagram 208. The anatomical diagram 208 may include a visual depiction of an anatomical zone of a human body, such as a torso, upper body, head, lower body, pelvic region, and/or an entire body. The anatomical diagram 208 may further include one or more boxes, each box representing a specific region of anatomy in the anatomical zone. Selection of one of the boxes results in findings associated with that specific region of anatomy being displayed, as will be described in more detail below. The anatomical diagram 208 may not include all possible anatomy, and thus the anatomical zone represented by the anatomical diagram 208 may be selected based on a type of exam being performed. For example, the exam may be an abdominal scan where the patient's internal organs in the abdominal region may be scanned ultrasonically. The operator, prior to scanning, may enter an input indicating that the exam is an abdominal exam, such as by selecting abdominal exam as a diagnosis category from a setting directory assigned to one button of the plurality of buttons 206.

As shown in FIGS. 2A-5C, the boxes of the anatomical diagram 208 may be oriented relative to one another to resemble a positioning of the represented anatomical regions with respect to the physical positioning of the regions in the human body. As shown in a magnified view 250 of FIG. 2B, a first anatomical region 220 of the anatomical diagram 208 is selectable via a virtual button. The virtual button representing the first anatomical region 220 may include a graphical representation of the first anatomical region, e.g., a kidney. Selecting the virtual button representing the first anatomical region 220 with the cursor 212 or other suitable input may result in appearance of a first tier 209 of icons of a first set of findings icons 210 positioned above the anatomical diagram 208.

Figure 2B:
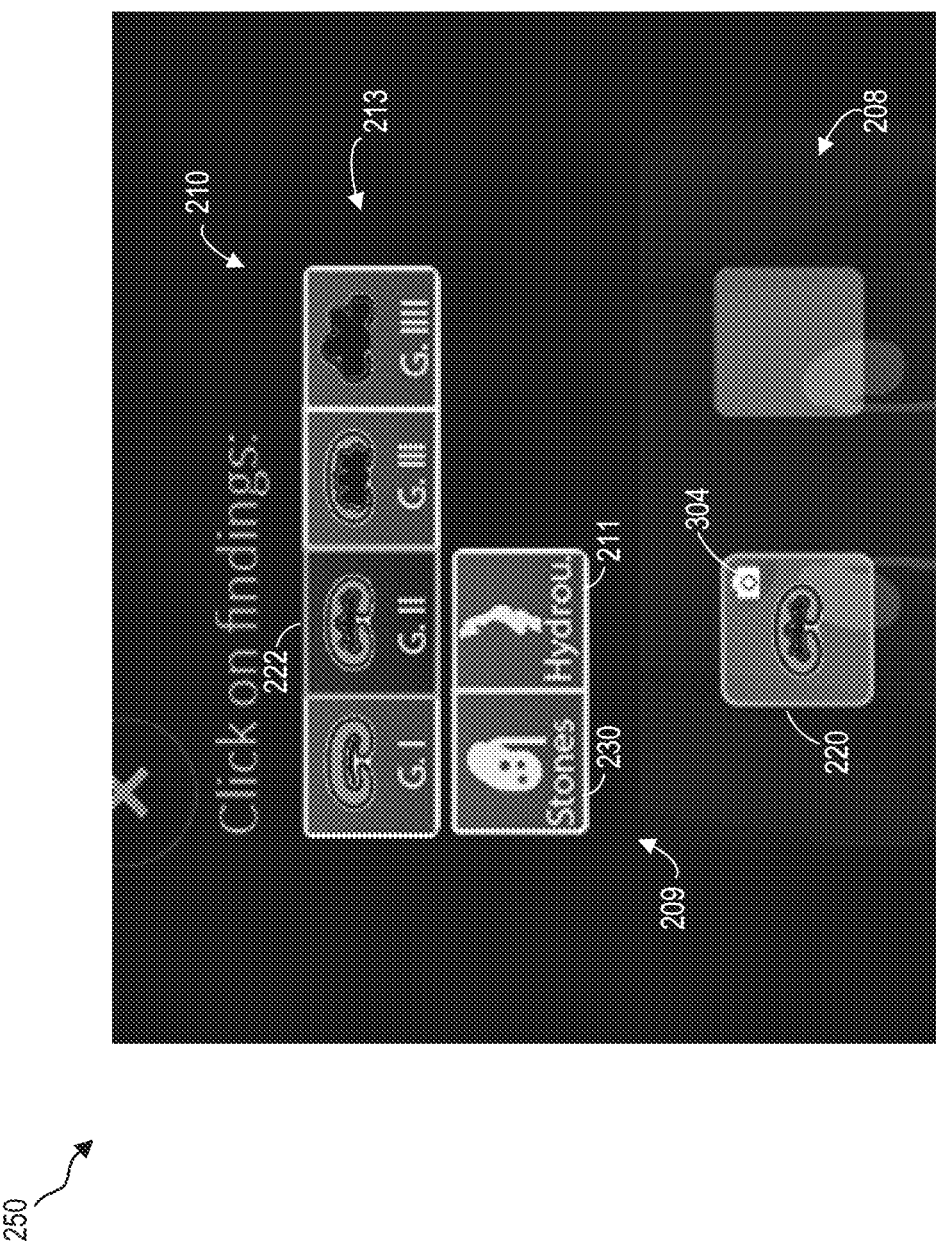
FIG. 2B shows an expanded view of a region of the display area of FIG. 2A.

As shown in FIG. 2B, the first tier 209 of icons may include several possible findings related to the kidney/adrenal glands, such as kidney stones and hydronephrosis. Each icon of the first tier 209 of icons may include a graphical illustration of diagnostic finding. For example, selection of a first icon 211 from the first tier 209 may result in display of a second tier 213 of icons. The first icon 211, may include a symbol denoting hydronephrosis.

The second tier 213 of icons represents a graded level of the selected finding. For example, as shown in FIG. 2B, the second tier 213 includes four icons, each representing a grading of hydronephrosis and each including a schematic illustration representative of the grading associated with the icon. For example, a second icon 222 representing a hydronephrosis grading of two may depict the kidney to be more occluded than an icon to the left, showing a grading of one, but less occluded than an icon to the right, showing a grading of three. Selection of the second icon 222 may result in a finding of grade II hydronephrosis to be saved for the patient undergoing the exam (e.g., in the patient's medical record) and also may result in the associated image (image 204) being saved. Further, once a finding is selected, that finding is displayed in a findings list 302, as shown in FIG. 3A in a second view 300 of the display area 202.

First tier 209 also includes a second icon 230 depicting a finding of kidney stones. Selection of second icon 230 may result in a different second tier of icons being displayed. The different second tier may be displayed in a same location as the second tier 213, and may represent possible findings related to kidney stones, such as grades of kidney stones. In this way, the first tier of icons may represent different classes of findings (kidney stones, hydronephrosis) and the second tier of icons may represent grades or other detailed findings that belong to the selected class of findings. Each class of findings may be associated with different grades of findings, such that selection of different classes results in different findings/grades being displayed. Likewise, different anatomical regions may be associated with different findings, such that selection of different anatomical regions results in different findings/classes of findings being displayed (other than redundant anatomical regions such as the kidneys). Additionally, some types of findings, such as gallstones, may not include associated grades but may instead include presence or absence. In such examples, selection of the gallstone finding icon may result in the finding being saved and displayed and the image being saved, without further input.

Figure 3A:
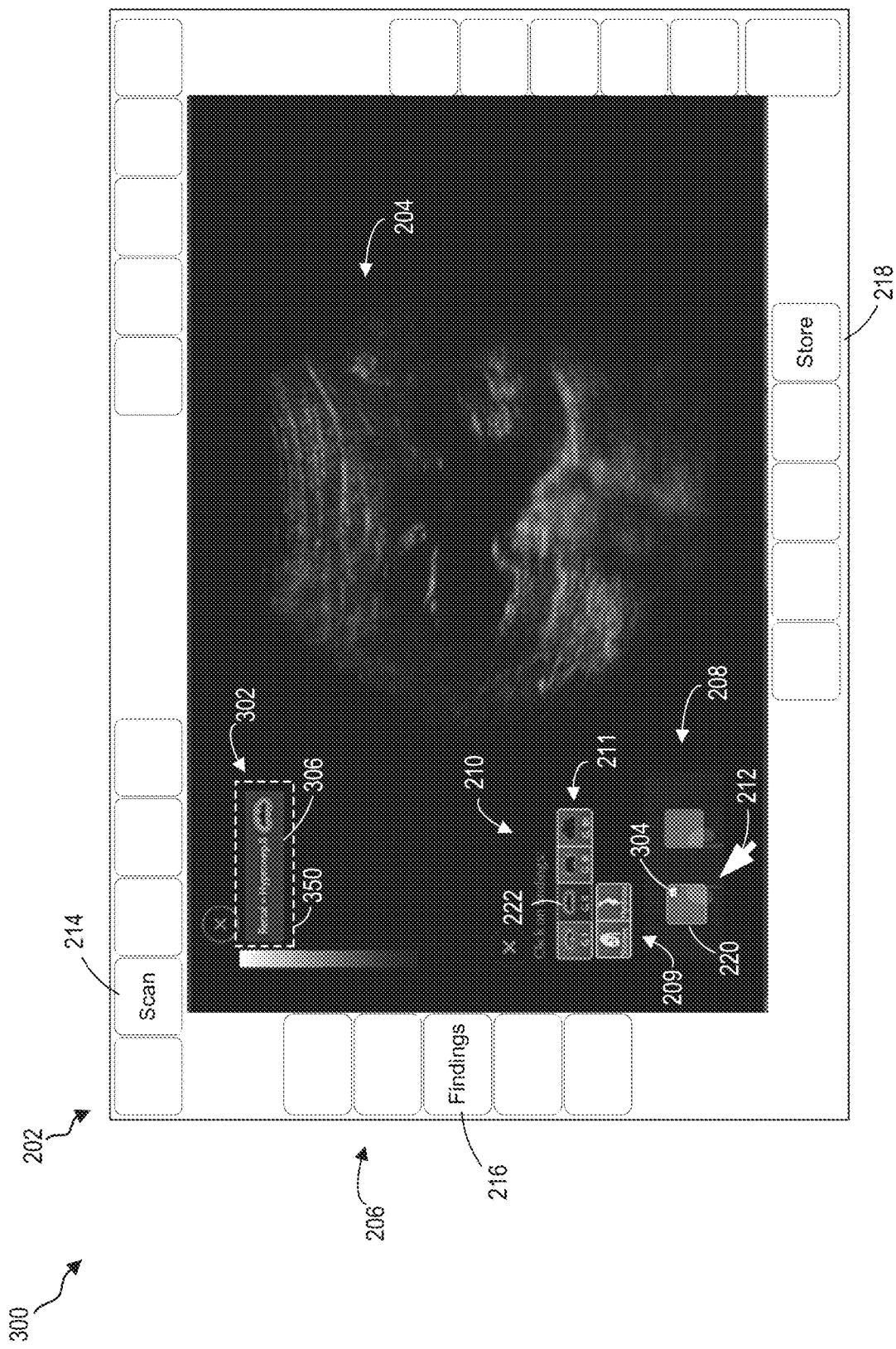
FIG. 3A shows a second view of the display area of the ultrasound imaging system.
Figure 3B:
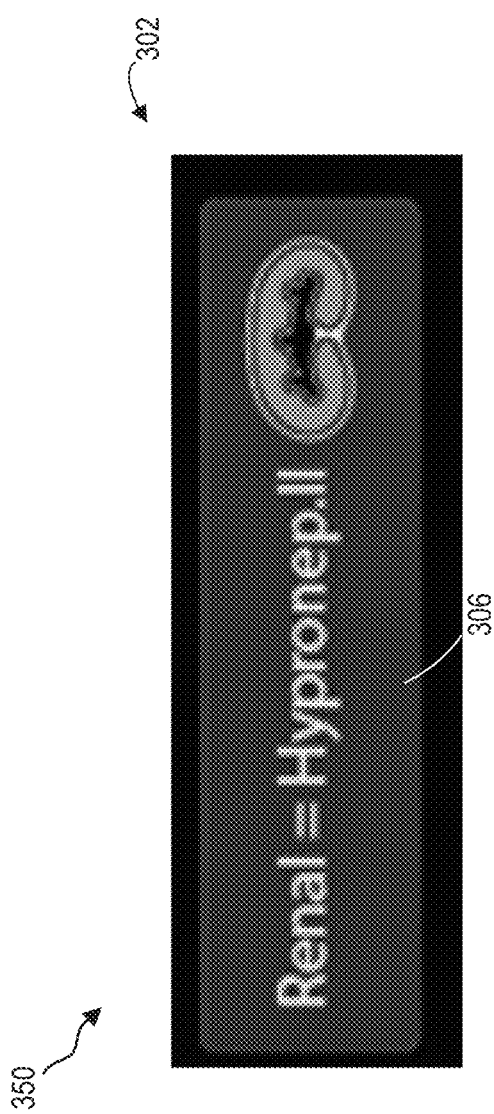
FIG. 3B shows an expanded view of a region of the display area of FIG. 3A

Referring now to FIG. 3A and magnified view 350 of FIG. 3B, the findings list 302 includes a first diagnostic finding 306, for example, of grade two hydronephrosis. As mentioned above, the image 204 may be automatically saved in response to selection of the second icon 222. The image may be associated with the finding, e.g., the image may be annotated or otherwise include information (e.g., in a header of the image) indicating that image includes a depiction of the selected finding. To notify the user that a finding has been selected and an image has been saved that is associated with the first anatomical region, the virtual button representing the first anatomical region 220 may be modified with one or more symbols. For example, a camera symbol 304 (or other suitable symbol, such as am image symbol, a number, etc.) may be displayed on the virtual button representing the first anatomical region 220 to denote an image has been saved with a finding relating to anatomy within the first anatomical region. Likewise, the virtual button representing the first anatomical region 220 may include a schematic representation of grade II hydronephrosis to denote the selection of the finding.

Figure 4A:
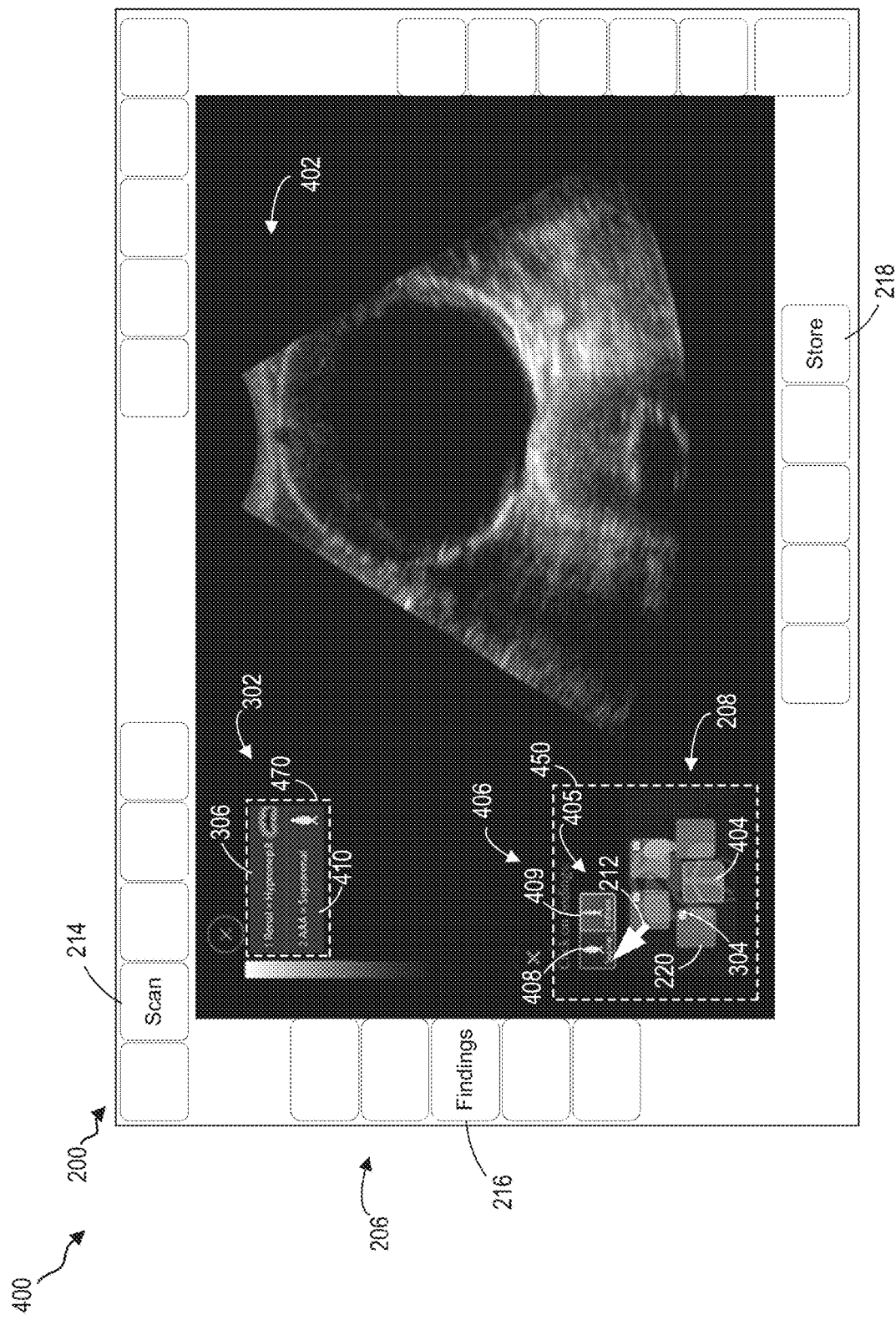
FIG. 4A shows a third view of the display area of the ultrasound imaging system.

Generation and storage of additional ultrasound images to the digital archive containing ultrasound images assigned to the patient may be conducted by scanning the patient, e.g., selecting the Scan button 214 and transmitting and receiving ultrasonic signals at the ultrasound transducer. A new, second diagnostic image 402 may be generated and displayed in the display area 202, as shown in a third view 400 of the display area 202 in FIG. 4. The second diagnostic image 402 may be an image of an anatomical region of the patient not included in the anatomical diagram 208 of FIGS. 2A-3C, and thus the operator may enter an input to notify the system that a different part of the anatomy is being scanned/examined. As an example, the operator may select an alternate region in the anatomical diagram 208, below and to a right-hand side of the first anatomical region 220, as indicated by cursor 212 in FIG. 3A. Selection of the alternate region may result in more or different anatomical regions being displayed in anatomical diagram 208, such as a second anatomical region 404, as shown in FIG. 4A. The second anatomical region 404 may represent an abdominal aortic region of the patient. In other examples, the system may automatically determine that different anatomy is being scanned, e.g., via image recognition performed on the acquired ultrasound images or via monitored progress through an automatic or semi-automatic imaging protocol.

Figure 4C:
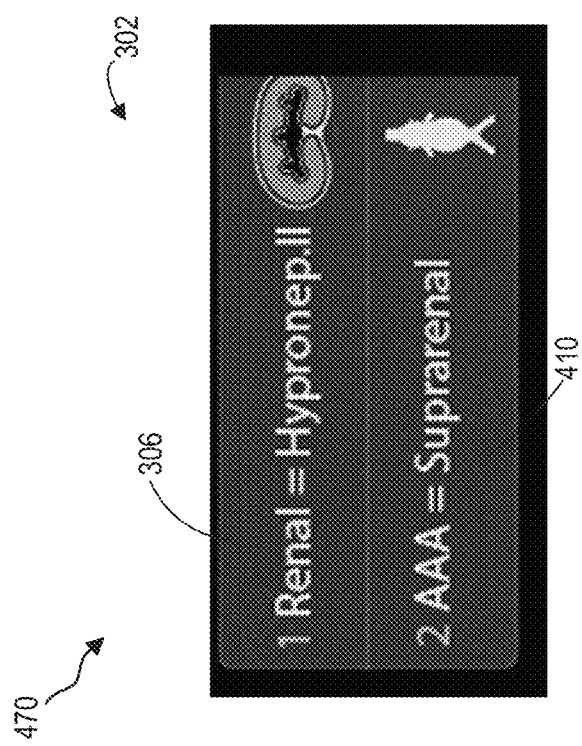
FIG. 4C shows an expanded view of a second region of the display are of FIG. 4A.
Figure 4B:
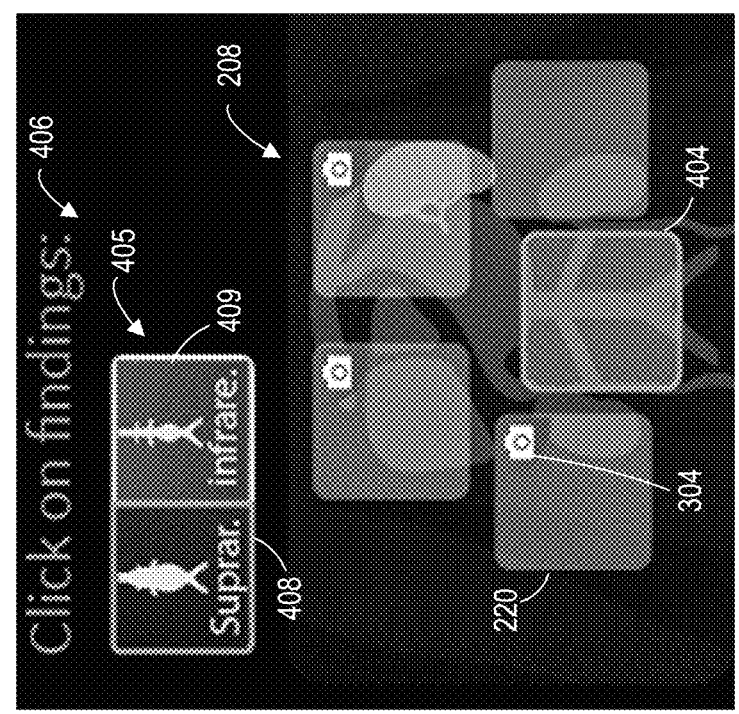
FIG. 4B shows an expanded view of a first region of the display area of FIG. 4A.
Figure 5C:
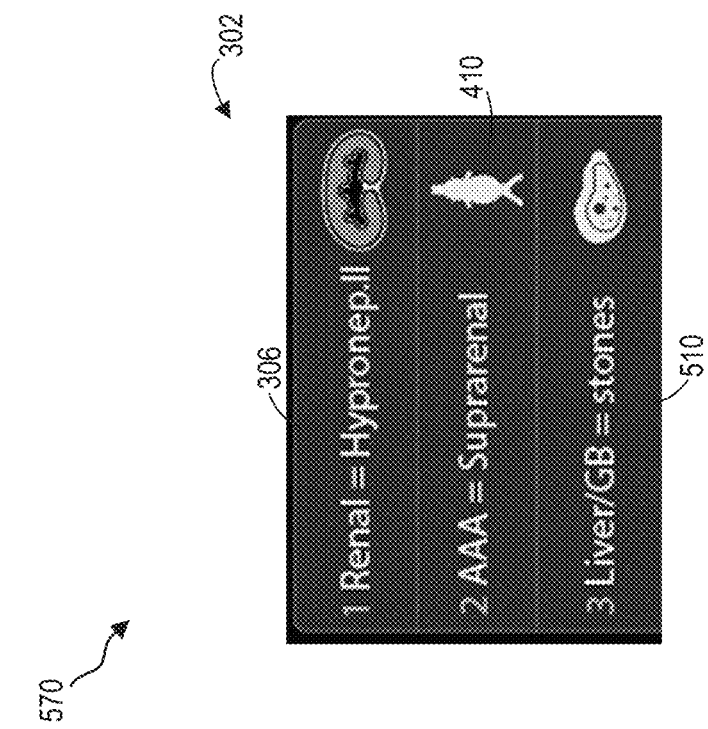
FIG. 5C shows an expanded view of a second region of the display are of FIG. 5A.
Figure 5B:
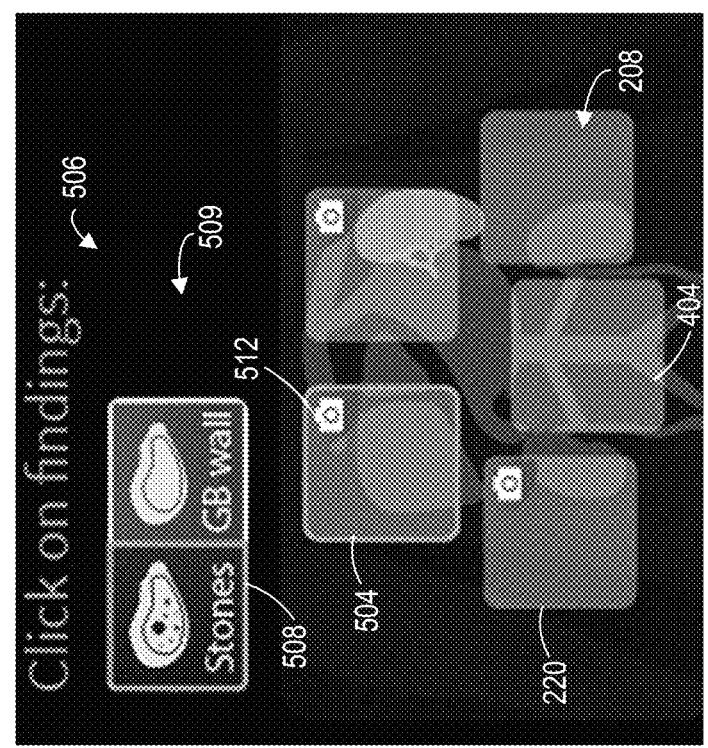
FIG. 5B shows an expanded view of a first region of the display area of FIG. 5A.

Turning now to FIGS. 4A-4C, the third view 400 of the display area 202 depicts a second set of findings icons 406, including two icons representing two diagnostic findings shown in a first tier 405 of icons for the second set of findings icons 406. The second set of findings icons 406 may be displayed in response to selection of a virtual button representing the second anatomical region 404. In the second set of findings icons, unlike the first set of findings icons 210 of FIGS. 2A and 3A, the diagnostic findings do not include graded levels. Instead, each icon of the first tier 405 of icons may represent a classification within a type of finding. For example, as shown in a first magnified view 450 of FIG. 4B, the first tier 405 includes a first icon 408 indicating presence of suprarenal abdominal aortic aneurysm and a second icon 409 indicating presence of infrarenal abdominal aortic aneurysm. As such, selection of either the first icon 408 or the second icon 409 does not result in display of a second tier of icons depicting graded levels of severity.

The first icon 408 may be highlighted upon selection, and the second diagnostic image 402 is saved in memory and linked to finding represented by the first icon 408. A symbol, such as the camera symbol 304 included in the virtual button representing the first anatomical region 220, may appear on the virtual button representing the second anatomical region 404 (not shown in FIG. 4B). A second diagnostic finding 410 associated with the first icon 408 may be added to the findings list 302, as shown in a second magnified view 470 of FIG. 4C.

The second diagnostic image 402 may be stored in the digital archive and linked to the second anatomical region 404 automatically upon the user selecting the first icon 408. When retrieved, the second diagnostic image 402 may display the findings list 302 as a summary of all diagnostic findings determined for the patient prior to and up to scanning of the selected anatomical region as saved in the archive. In other examples, any prior or subsequent findings may not be displayed with the second image.

An additional ultrasound image, also scanned from the abdominal region of the patient, may be added to the patient's digital medical archive, as shown in FIG. 5A. In FIG. 5A, a third diagnostic image 502 acquired from the ultrasound transducer is depicted. The third diagnostic image 502 may be an image of a third anatomical region 504 included in the anatomical diagram 208, obtained by selecting the Scan button 214 and scanning the patient with the ultrasound transducer. Selection of a virtual button representing the third anatomical region 504 causes display of a third set of findings icons 506, as shown in a first magnified view 550 of FIG. 5B, that includes a first tier 509 of icons with two findings icons representing diagnostic findings associated with the third anatomical region 504.

The first icon 508 may represent for example, presence of stones in the gallbladder. A diagnostic finding assigned to the first icon 508 may be added as a third diagnostic finding 510 to the findings list 302 (shown in a second magnified view 570 of FIG. 5C) and associated with the third diagnostic image 502 if the first icon 508 is selected. The third image 502 may be automatically stored in response to selecting the first icon 508. The storage of the third diagnostic image 502 may be indicated by a camera symbol 512 on the virtual button representing the third anatomical region 504, as the third image 502 includes anatomy that is represented by the third anatomical region 504.

During an exam, or after an exam has been completed, saved images may be retrieved in an easy and intuitive manner via the anatomical diagram. For example, as explained above, the virtual buttons that are included in the anatomical diagram may include a symbol, e.g., the camera symbol 512 in FIG. 5B, if one or more images associated with that anatomical region are saved, to indicate that one or more images are stored and linked to the anatomical region. By selecting a button having the symbol, a linked diagnostic image may be automatically displayed. The diagnostic image, as described above, may include a findings list summarizing graded diagnostic findings determined from the ultrasound images obtained for the patient. In some examples, if more than one image is associated with a given anatomical region, each image may be displayed (e.g., as thumbnails or as a navigable slide show) when the virtual button is selected. During an exam, if a user wishes to view images that have already been saved, the user may select the symbol (e.g., the camera symbol) on the virtual button. Once an exam is complete, if a user wishes to view images saved during the exam, a graphical user interface that includes the anatomical diagram may be displayed and the user may select images to view by selecting a desired anatomical region.

Ultrasound images may be readily saved and organized in real-time during operation of the ultrasound imaging system via a simple and efficient process based on graphical, interactive images rather than searching through text-based lists. The graphic-based image archiving described above may be applied to various types of diagnostics scanning. As one example, as shown in FIG. 3A, ultrasound imaging may be used to evaluate hydronephrosis and assess a severity of hydronephrosis according to a grading scale of one to four. In another example, the graphic-based image archiving may be applied to diagnosing lung conditions, which will be explained in more detail below with respect to FIGS. 8A and 8B. In yet another example, a patient's heart may be scanned for diastolic dysfunction. Diastolic dysfunction may be graded according to four levels of severity.

FIG. 8A illustrates a first view 800 of display area 202 during a different diagnostic exam performed with the ultrasound system. In the example illustrated in FIG. 8A, a diagnostic lung exam is/has been performed, and thus an image 802 of a lung is displayed in display area 202. Image 802 is an example of an image that may be acquired by the ultrasound imaging system during the lung exam. In response to a request to document one or more findings, an anatomical diagram 804 is displayed in display area 202. Further, FIG. 8A illustrates a plurality of icons 806 that may be displayed in response to selection of control button displayed as part of anatomical diagram 804.

Image 802 includes a plurality of B lines, which are comet-tail image artifacts that are indicative of subpleural interstitial edema. An operator, such as a sonographer, may annotate an image to assist in identification and/or quantitation of the B lines. Image 802 includes a plurality of annotations, such as annotation 803, which may be used to determine the number of B lines and/or other information about the B lines (e.g., extent, angle, etc.).

Figure 8B:
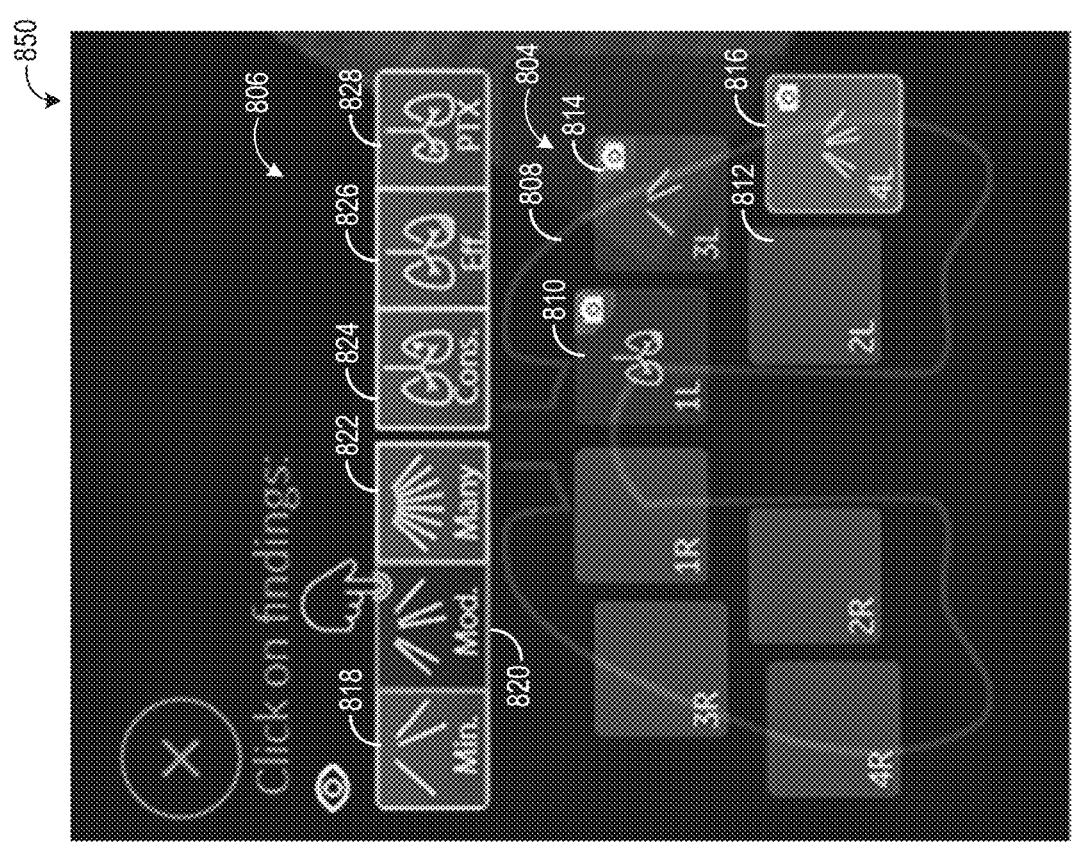
FIG. 8B shows an expanded view of a first region of the display area of FIG. 8A.

A magnified view of region 850 of display area 202 is shown in FIG. 8B. As shown in FIG. 8B, anatomical diagram 804 includes a representation 808 of the anatomical zone currently being imaged/examined, which in the case of FIG. 8B is the lungs. Representation 808 includes a line drawing depicting the shape of the anatomical zone, but other configurations are possible without departing from the scope of the disclosure. Anatomical diagram 804 further includes a plurality of control buttons. Each control button represents a different region of the anatomical zone represented in anatomical diagram 804. As shown in FIG. 8B, the plurality of control buttons includes four control buttons for each lung. For example, the left lung includes a first control button 810, a second control button 812, a third control button 814, and a fourth control button 816. The right lung includes equivalent control buttons. Each control button is positioned over the representation 808 at a location that corresponds to the anatomy represented by that control button, e.g., first control button 810 is positioned over a top right portion of the left lung and thus represents that region of the anatomical zone.

User selection of a control button of anatomical diagram 804 may trigger display of a second plurality of control buttons (herein referred to as a plurality of icons) that represent diagnostic findings that are associated with the anatomy represented by the selected control button of the anatomical diagram. As shown in FIG. 8B, a user has selected the fourth control button 816, triggering display of the plurality of icons 806. The plurality of icons 806 includes six icons. A first subset of the plurality of icons 806 includes a first icon 818, a second icon 820, and a third icon 822, each representing a different grading (e.g., level) of B lines present in the diagnostic image(s) representing the selected anatomic region (e.g., the region represented by the fourth control button 816). The first icon 818 represents a minimal amount of B lines, the second icon 820 represents a moderate amount of B lines, and the third icon 822 represents a high amount of B lines (e.g., many B lines). A second subset of the plurality of icons 806 includes a fourth icon 824, a fifth icon 826, and a sixth icon 828, each representing the presence of different findings related to the lungs. For example, the fourth icon 824 represents consolidation, the fifth icon 826 represents pleural effusions, and the sixth icon 828 represents pneumothorax.

User selection of an icon of the plurality of icons 806 results in the finding associated with the icon being associated with the patient's diagnostic exam. For example, the finding may be saved in a report that will be saved as part of the patient's medical record and the finding may be displayed on the display area (e.g., in a list of findings). Further, the selection of an icon results in the associated diagnostic image (e.g., the image which includes the finding identified by the clinician, such as image 802) being saved in permanent memory (e.g., as part of the report in the patient's medical record and/or on memory included as part of a PACS, RIS, etc.). Additionally, at least in some examples, user selection of an icon may result in an annotation being displayed within the associated control button to notify/remind the user that one or more findings have been already been documented. For example, selection of the second icon 820 causes display of an annotation within the fourth control button 816. As shown, the annotation includes a storage symbol indicating an image has been saved for that control button/anatomical region, herein in the form of a camera symbol. The annotation further includes a representation of the finding, e.g., a diagram/pictorial representation of a moderate amount of B lines. In the example shown in FIG. 8B, an annotation is displayed within the third control button 814, indicating that a finding was selected for the anatomical region represented by the third control button (e.g., a minimal amount of B lines) and an annotation is displayed in the first control button 810, indicating that a finding was selected for the anatomical region represented by the first control button (e.g., pleural effusions).

In this way, a diagnostic finding, and in some examples a grading of a diagnostic finding, may be selected with only one or two inputs (at least once the anatomical diagram is displayed) and without having to navigate through nested text-based menus. Each finding/grading may be displayed in graphical form as tiled icons, for example, which may enable rapid identification of and differentiation among different findings. The different diagnostic findings may be grouped by anatomy, which may allow display of the most relevant findings for a given anatomical region. Once a finding is selected, the user may be reminded of that finding via annotations displayed within the anatomical diagram.

It will be appreciated that the display area 202 shown in FIGS. 2A-5C, 8A, and 8B is a non-limiting example and variations in a configuration of the display area have been contemplated. For example, relative positioning of elements shown in the display area may be different from that shown. The diagnostic image may be to left of the anatomical diagram instead of to the right, the anatomical diagram may be in an upper right corner of the display area, and/or the findings list may be located in different region of the diagnostic image. The graphical icons and buttons shown as squares and rectangles may instead be circular, elliptical, or some other shape. As well, relative sizes of the display area elements may be varied without departing from the scope of the present disclosure. Further, while the present description has been provided with reference to ultrasound images, it is to be understood that the graphical grading described herein may be performed using images obtained with other imaging modalities, such as magnetic resonance imaging, x-ray, etc.

Medical images may be automatically stored when an operator selects a diagnostic finding, represented by graphical icons and/or virtual buttons on a display area of an ultrasound imaging system. An example of a method 600 is shown in FIG. 6 for storing ultrasound images linked to a graphical icon representing a graded diagnostic finding. In particular, method 600 relates to saving an ultrasound image acquired from an ultrasound scan with information pertaining to a diagnostic finding determined from the ultrasound image. Method 600 is described with regard to the systems and components of FIG. 1, though it should be appreciated that the method may be implemented with other systems and components without departing from the scope of the present disclosure. Method 600 may be implemented as executable instructions in non-transitory memory, such as memory 120, and executed by a processor, such as processor 116, of the system 100 and displayed on a display area of a display device, such as the display area 202 of FIGS. 2A-5C, 8A, and 8B. Method 600 may be initiated by an operator, such as a physician or medical personnel, such as sonographers.

Method 600 beings at 602. At 602, an indication of an exam type is received. For example, an operator may use an input device, such as a mouse, stylus, or touchpad, to position a cursor over a Settings icon, button, or tool. The input device may alternatively be the operator's finger if the display area is adapted to be a touch screen. A list of possible exam types may be displayed, including internal organs, muscle tissues, vessels, tendons, etc. and the operator may click on the desired exam type, instructing the processor to load settings suitable for the type of exam. In some examples, the exam types may include diagnostic exams, such as an echocardiogram, a fetal ultrasound, etc., in addition to or rather than specific anatomy.

Method 600 continues to 604 to acquire image information of a patient using an ultrasound transducer. The ultrasound transducer transmits ultrasonic signals while scanning the patient and receives reflected signals. The acquired data may be processed, at 606, into a graphical image by the processor and displayed in the display area of the display device. The graphical image may include an image obtained from the ultrasonic signal and may also include an interactive anatomical diagram, such as the anatomical diagram 208 of FIGS. 2A-5B and/or the anatomical diagram 804 of FIGS. 8A and 8B. The anatomical diagram may display a specific zone of a human body, such as a torso, a set of lower limbs (e.g., legs), etc., where the specific area that is displayed is selected based on the type of exam chosen by the operator. The anatomical diagram may have boxes highlighting specific anatomical regions of the displayed zone, such as kidneys, a liver, a heart, etc., when the zone of the body (e.g., torso) is displayed.

At 608, the method includes determining if a selection of an anatomical region from the anatomical diagram is received. The anatomical region may be selected by the operator by, for example, placing the cursor over the box highlighting a desired anatomical region and pressing a button on the input device. If no selection is detected, the method continues to 610 to wait for further instructions before performing any subsequent actions. While waiting for further instructions, the ultrasound image and anatomical region may continue to be displayed. In some examples, if a selection has not been received after a threshold amount of time has elapsed, a prompt may be displayed to prompt the operator to make a selection or change the displayed anatomical region, for example. The method then returns to the start.

If an anatomical region is selected from the anatomical diagram, the method proceeds to 612 to display one or more findings icons, each icon representing either a graded severity of the diagnostic finding or a presence of the diagnostic finding. For example, the anatomical region selected may be a heart and the plurality of findings icons may include four icons each representing a different level of diastolic dysfunction. In other examples, such as selection of a gallbladder in the anatomical diagram, the plurality of findings icons may not include gradings but instead may indicate a presence or absence of an obstruction. In such an example, two findings icons may be shown, one indicating gallstones are present and one indicating an absence of gallstones. Further, in some examples only one icon relating to gallstones may be displayed, an icon indicating a presence of gallstones.

In other examples, the anatomical diagram may include several different types of diagnostic findings. As such, the findings icons may include classes of findings, e.g., the icons may be displayed in tiers. For example, a first tier of findings icons may be displayed when an anatomical region is selected, the first tier of findings icons presenting a list of findings classes. Selecting an icon from the first tier of findings icons displays a second tier of findings icons, the second tier corresponding to gradings associated with the class of diagnostic finding selected from the first tier. As an example, selecting an anatomical region in the anatomical diagram representing a heart may trigger display of a first tier of findings icons including a first icon for diastolic dysfunction, a second icon for wall thickness, and a third icon for valve function. Selecting the first icon results in display of a second tier of findings icons, each icon representing different graded levels of diastolic dysfunction.

The plurality of findings icons shown in the display area may not be an exhaustive list but instead may be a list of selected diagnostic findings. In some examples, the findings icons that are depicted may represent the most common findings for a given anatomy and/or type of exam being performed. In some examples, the findings icons depicted in the first tier and/or second tier upon selection of the anatomical region of the anatomical diagram may be customizable based on operator preference, anticipated diagnoses for a patient, etc. The operator may select a Findings button, e.g., the Findings button 216 of FIGS. 2A-5A and 8A, which may result in display of a list of all possible diagnostic findings that may be determined by ultrasound imaging. By choosing a diagnostic finding from the list, the selected diagnostic finding may be displayed as one of findings icon presented when the operator clicks on the anatomical region of the anatomical diagram. Such a procedure may be performed during an exam, as described. In other examples, a user may predefine which findings will be displayed prior to an exam being conducted.

At 614, the method includes determining if an icon of the plurality of findings icons is selected. The icon may be selected by the operator by, for example, placing the cursor over the icon and pressing a button on the input device. If no icon is selected, the method continues to 616 to await further commands from the operator.

If an icon is selected, method 600 proceeds to 618 to store the ultrasound image in a digital archive of ultrasound images and associate the image with the selected finding. Once saved, the ultrasound image may be linked to the selected findings icon so that clicking on the icon (or a symbol of the icon) automatically displays the ultrasound image. Linkage of the image to the icon may be indicated by a graphical symbol appearing on the findings icon, such as a camera symbol, photo symbol, or other suitable symbol.

The displayed image, once linked to the icon, may also present a findings list that displays medical diagnoses determined for the patient during an ultrasound imaging session, including the finding represented by the selected icon. The method then returns to the start.

Thus, method 600 provides for a graphical grading system where a user may select one or more icons indicative of diagnostic findings of a patient. The icons may include graphical/schematic representations of the associated findings and may be displayed along with a diagnostic image from which the findings may be identified. Selection of an icon may result in the finding indicated by the icon being saved in a report for the patient's medical record. Additionally, selection of an icon may result in the associated diagnostic image being saved in the report and/or in permanent storage. The icons may be organized/displayed by anatomical region and/or findings class. For example, an anatomical diagram may be displayed that includes multiple anatomical regions of interest (e.g., being scanned during the exam). Selection of a region may result in findings associated with that region being displayed. In some examples, the anatomical region may include multiple classes of findings, and thus icons representing classes of findings may be displayed, and icons representing actual findings (graded levels, presence or absence, etc.) may be displayed in response to a class of findings being selected. The anatomical diagram and tiers/sets of icons may be displayed together and in a logical manner (e.g., mimicking the underlying anatomy) along with the diagnostic image. To reduce visual clutter, the findings that are displayed via the graphical grading system may be a limited set of findings selected from a more exhaustive list of possible findings. The displayed findings may be chosen based on highest likelihood of being selected (e.g., most common findings) and/or based on user preference.

In some examples, as a user progresses through an exam, a selected finding may dictate which subsequent findings are displayed to the user via the graphical grading system. For example, if a user selects a finding of hydronephrosis, an icon representing kidney stones may also be displayed, or displayed subsequently, as kidney stones may be a likely cause of the hydronephrosis.

While method 600 is described above as being executed while an ultrasound scanning session is underway, in some examples the graphical grading system described herein may be executed after the scanning session is complete. For example, a physician may analyze a set of images obtained by a sonographer and identify findings from the images, after the imaging session is complete. The anatomical diagram and sets of icons as discussed above may be displayed with each image, to enable selection of findings and storage of desired images with fewer inputs and in faster manner than previous systems.

A stored ultrasound image may also be retrieved via linking the archived image to a findings icon. A flow chart is shown in FIG. 7, illustrating a method 700 for image retrieval from an ultrasound imaging system. Similar to method 600, method 700 may be implemented as executable instructions in non-transitory memory, such as memory 120, and executed by a processor, such as processor 116, of the system 100 and displayed on a display area of a display device, such as the display area 202 of FIGS. 2A-5C, 8A, and 8B.

Method 700 begins at 702. At 702, the method includes displaying an anatomical diagram for a selected patient. The anatomical diagram may be displayed during an imaging session/exam, as explained above with respect to FIG. 6. In other examples, the anatomical diagram may be displayed in response to a request from a user, such as when the user desires to view a report of an exam that has already been conducted.

At 706, the method determines if an anatomical region of the anatomical diagram is selected. The anatomical region may be selected by the operator by, for example, placing a cursor over a box highlighting a select anatomical region and pressing a button on an input device, or other suitable input mechanism. In some examples, the selection of the anatomical region may include selection of a symbol, such as a camera symbol, indicating that images associated with that anatomical region have been saved. An operator may be searching for a particular image, e.g., for an ultrasound image of a kidney showing hydronephrosis, that the operator previously obtained during an ultrasound imaging session and may select a box representing the kidney. Alternatively, the operator may be assessing an overall state of health of the patient and surveying some or all images acquired and saved to provide a complete diagnosis.

If selection of an anatomical region is not detected, the method continues to 708 to wait for further commands from the operator. The method then returns to the start. If an anatomical region is selected, the method proceeds to 710 to display one or more images associated with the selected anatomical region. The images may be displayed as thumbnails, particularly if multiple images have been saved for that anatomical region. In some examples, the images may be displayed individually and the operator may scroll through or click through the images. In some examples, displayed image(s) may also include a findings list that displays medical diagnoses determined for the patient during an ultrasound imaging session, including the finding(s) represented in the displayed image. If a selected anatomical region includes multiple images that are associated with different findings, the images may be organized by finding. In such examples, findings icons may be displayed, as explained above with respect to FIG. 6, and then images associated with a giving finding may be displayed upon selection of the finding icon. The method then returns to the start.

In this way, graphical grading of medical diagnostic findings obtained by ultrasound imaging may be efficiently stored in real-time during an ultrasound imaging session via a simple process with minimal steps. An ultrasound image may be saved with diagnostic information by selecting an anatomical region from an anatomical diagram followed by selection of a suitable findings icon, the icon representing a graded diagnostic finding. The image is automatically stored upon selection of the findings icon and subsequently retrievable by re-selecting the findings icon. A number of steps included in storing ultrasound images in an organized matter with relevant diagnostic information is thereby reduced, increasing operational efficiency and workflow and decreasing a likelihood of incorrect storage of images as well as reducing a likelihood that the operator neglects to save an acquired image prior to commencing a new ultrasound scan.

The technical effect of graphical grading of ultrasound information includes storing an ultrasound image to a digital archive coupled to a graphical icon representative of the diagnostic grading. Another technical effect of the disclosure includes a reduction of interactions with a display area to store the image. Yet another technical effect is a reduction in time between ultrasound scans. Yet another technical effect is a decrease in interactions and time for retrieving a stored ultrasound image.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method executable by a processor of a system by executing instructions stored in non-transitory memory of the system, the method comprising:
    displaying an acquired medical image of a subject on a display area of a display device of the system;
    displaying a virtual anatomical diagram on the display area adjacent to the medical image, the virtual anatomical diagram including a visual depiction of an anatomical zone of a body, the anatomical zone selected from a plurality of possible anatomical zones based on a type of exam being performed on the subject and/or based on anatomical features present in the medical image;
    responsive to a first user input including selection of an anatomical region from the anatomical zone included in the anatomical diagram, displaying a plurality of icons, each icon of the plurality of icons representing a respective diagnostic finding associated with the anatomical region while the anatomical diagram and medical image are still displayed; and
    responsive to a second user input including selection of an icon of the plurality of icons, associating a diagnostic finding represented by the selected icon with the medical image and storing the medical image with the associated diagnostic finding in permanent memory.

2. The method of claim 1, further comprising displaying a symbol on the selected anatomical region of the anatomical diagram upon storing the image, and wherein the second user input is a single input such that the diagnostic finding is associated with the medical image responsive to the single input.

3. The method of claim 2, further comprising, after the medical image has been stored, and responsive to selection of the symbol, displaying the medical image.

4. The method of claim 1, further comprising displaying the diagnostic finding corresponding to the selected icon in a list displayed on the display area, the list displayed while the anatomical diagram and the medical image are still displayed.

5. The method of claim 1, wherein the displaying the virtual anatomical diagram includes displaying a plurality of virtual buttons, each button representing a different anatomical region, wherein the first user input selecting the anatomical region is a selection of one of the plurality of virtual buttons, and wherein selection of different virtual buttons results in display of different pluralities of icons representing different diagnostic findings.

6. The method of claim 5, wherein displaying the plurality of virtual buttons includes selecting the plurality of virtual buttons from among a plurality of possible virtual buttons each representing a different diagnostic finding based on a prevalence of each diagnostic finding.

7. The method of claim 1, wherein displaying the plurality of icons representing diagnostic findings associated with the anatomical region comprises displaying a first set of icons of the plurality of icons, the first set of icons representing different classes of diagnostic findings associated with the anatomical region.

8. The method of claim 7, wherein displaying the plurality of icons representing diagnostic findings associated with the anatomical region comprises displaying a second set of icons of the plurality of icons in response to a selection of an icon of the first set of icons, the second set of icons representing findings within a selected class of findings associated with the first icon.

9. The method of claim 1, wherein displaying the plurality of icons representing diagnostic findings associated with the anatomical region comprises displaying a first set of icons and a second set of icons, the first set of icons representing diagnostic findings associated with the anatomical region and the second set of icons representing graded levels of a selected diagnostic finding, wherein selection of a given icon of the second set of icons results in a selected graded level of the diagnostic finding being associated and stored with the image.

10. An ultrasound imaging system, comprising:
    an ultrasound transducer;
    a display device with a display area; and
    a processor configured with instructions in non-transitory memory that when executed cause the processor to:
        acquire ultrasound data of a subject via the ultrasound transducer;
        display the ultrasound data as an image on the display area of the display device with a virtual anatomical diagram, the virtual anatomical diagram including a visual depiction of an anatomical zone of a body, the anatomical zone selected from a plurality of possible anatomical zones based on a type of exam being performed on the subject and/or based on anatomical features present in the image;
        responsive to detecting selection of a region from the anatomical zone included in the anatomical diagram, display a plurality of virtual icons, each icon representing a type of medical diagnostic finding specific to the region; and
        responsive to detecting selection of an icon from the plurality of virtual icons, associate a first medical diagnostic finding represented by the selected icon with the image and store the image and first medical diagnostic finding in a permanent memory, wherein the anatomical zone includes a kidney and the plurality of virtual icons includes a first icon representing hydronephrosis and a second icon representing kidney stones.

11. The ultrasound imaging system of claim 10, wherein the plurality of virtual icons is selectable from a list of diagnostic findings spanning a wider range of findings than the plurality of virtual icons and the plurality of virtual icons includes only a portion of the list of diagnostic findings.

12. The ultrasound imaging system of claim 10, wherein the instructions further include instructions to, after the image is stored and responsive to selection of the icon from the plurality of virtual icons, retrieve the image from the memory and display the stored image.

13. The ultrasound imaging system of claim 10, wherein the instructions further include instructions to, responsive to detecting selection of the icon, display a findings list on the display area, the findings list including the first medical diagnostic finding represented by the icon, and wherein the findings list, plurality of virtual icons, and the image are simultaneously displayed on the display area.

14. The ultrasound imaging system of claim 13, wherein the instructions further include instructions to, responsive to detecting selection of the icon, display a graphical representation of the first medical diagnostic finding within the icon.

15. The ultrasound imaging system of claim 10, wherein the anatomical diagram includes a graphical depiction of anatomy represented by the anatomical diagram and one or more control buttons positioned over the graphical depiction, and wherein detecting selection of the region includes detecting selection of a control button positioned at the region.

* * * * *